US012779226B2

(12) United States Patent
Burnam et al.

(10) Patent No.: US 12,779,226 B2
(45) Date of Patent: Nov. 3, 2026

(54) SYSTEM AND METHOD FOR NON-INVASIVE AUTONOMIC NERVE ACTIVITY MONITORING USING ARTIFICIAL INTELLIGENCE

(71) Applicant: BaroPace, Inc., Ashland, OR (US)

(72) Inventors: Michael Burnam, Ashland, OR (US); Eli Gang, Los Angeles, CA (US)

(73) Assignee: BaroPace, Inc., Ashland, OR (US)

( * ) Notice: Subject to any disclaimer, the term of this patent is extended or adjusted under 35 U.S.C. 154(b) by 416 days.

(21) Appl. No.: 18/258,475

(22) PCT Filed: Nov. 10, 2021

(86) PCT No.: PCT/US2021/058821
§ 371 (c)(1),
(2) Date: Jun. 20, 2023

(87) PCT Pub. No.: WO2022/139971
PCT Pub. Date: Jun. 30, 2022

(65) Prior Publication Data

US 2024/0299754 A1 Sep. 12, 2024

Related U.S. Application Data

(60) Provisional application No. 63/166,185, filed on Mar. 25, 2021, provisional application No. 63/150,480,
(Continued)

(51) Int. Cl.
*A61B 5/00* (2006.01)
*A61N 1/365* (2006.01)
*G16H 50/20* (2018.01)

(52) U.S. Cl.
CPC ................................ *A61N 1/36585* (2013.01)

(58) Field of Classification Search
CPC ............ A61N 1/36585; A61N 1/36114; A61N 1/3627; A61N 1/3628; A61N 1/36514;
(Continued)

(56) References Cited

U.S. PATENT DOCUMENTS 10,448,852 B2 10/2019 Chen et al.
2006/0106428 A1* 5/2006 Libbus ............... A61N 1/36114 607/23
(Continued)

FOREIGN PATENT DOCUMENTS

JP 2020521128 A * 7/2020 ......... A61B 5/02405
WO 2020096982 A1 5/2020
(Continued)

OTHER PUBLICATIONS

Translation of JP 20202521128 (Year: 2020).*
(Continued)

*Primary Examiner* — Brian T Gedeon
(74) *Attorney, Agent, or Firm* — DLA Piper LLP (US)

(57) ABSTRACT

A method of therapeutically treating a subject includes the steps of: sensing sympathetic nerve activity; communicating the sensed sympathetic nerve activity to a processor; using machine learning in the processor to identify input data sets correlated to a physiological end point in the subject by processing the input data input sets to experientially optimize an algorithmically defined physiological goal defined in output data sets by the machine learning; and dynamically controlling a therapeutic device in real time with the processor using the output data sets to treat the subject mediated by the therapeutic device by establishing or tending to establish the physiological end point in the subject.

20 Claims, 7 Drawing Sheets

Related U.S. Application Data filed on Feb. 17, 2021, provisional application No. 63/128,537, filed on Dec. 21, 2020.

(58) Field of Classification Search
CPC A61N 1/36139; A61B 5/0533; A61B 5/4035; A61B 5/4836; A61B 5/7267
See application file for complete search history.

(56) References Cited

U.S. PATENT DOCUMENTS

| | | | |
|---|---|---|---|
| 2019/0274655 | A1 | 9/2019 | Thakur et al. |
| 2019/0351238 | A1 | 11/2019 | Ternes et al. |
| 2020/0037887 | A1 | 2/2020 | Thakur et al. |
| 2020/0037888 | A1 | 2/2020 | Thakur et al. |

FOREIGN PATENT DOCUMENTS

| | | | |
|---|---|---|---|
| WO | 2020210060 | A1 | 10/2020 |
| WO | 2020240200 | A1 | 12/2020 |

OTHER PUBLICATIONS

International Search Report and Written Opinion issued in International Application No. PCT/US2021/, mailed on May 5, 2022.
Office Action for Israel Patent Application No. 303894 dated Oct. 29, 2025, 4 pages.
Office Action for CA Patent Application No. 3,205,940, dated Mar. 24, 2026, 5 pages.

* cited by examiner

1. Skin sensor
2. Machine learning module
3. Band pass filters
4. Pressure pace AI
5. Pacemaker
6. Pacemaker lead
7. Right atrium of Heart

SYSTEM AND METHOD FOR NON-INVASIVE AUTONOMIC NERVE ACTIVITY MONITORING USING ARTIFICIAL INTELLIGENCE

CROSS-REFERENCE TO RELATED APPLICATIONS

This is a National Stage Application under 35 U.S.C. § 371 of International Application No. PCT/US2021/058821, filed Nov. 10, 2021, now published as WO 2022/139971 A1, which claims priority to U.S. Provisional Patent Application No. 63/166,185, filed on Mar. 25, 2021, to U.S. Provisional Patent Application No. 63/150,480, filed on Feb. 17, 2021, and to U.S. Provisional Patent Application No. 63/128,537, filed on Dec. 21, 2020, the entireties of each of which are incorporated herein by reference.

BACKGROUND

Field of the Technology

The invention relates to the field of artificial intelligence or machine learning to control a therapeutic device or pacemaker according to sensed and processed sympathetic nerve activities and cardiac parameters.

Description of the Prior Art

Cardiac care is one particular area of medical treatment that heavily utilizes measurement of nerve activity. Activity in the autonomic nervous system controls the variability of heart rate and blood pressure. The sympathetic and parasympathetic branches of the autonomic nervous system modulate cardiac activity. Elevated levels of sympathetic nerve activity (SNA) are known to be correlated with heart failure, coronary artery disease, and may be associated with the initiation of hypertension. Sympathetic nerve activity is also thought to be important as a predictor of heart rhythm disorders, including sudden cardiac death. Therefore, a diagnostic index of "autonomic tone" produced in accordance with measurement of sympathetic nerve activity may have considerable clinical value. As known in the art, clinical utilization of autonomic nerve activity is mostly derived from therapeutic biochemical perturbations like the use of beta-blockers in high blood pressure management. While elevated levels of sympathetic nerve activity are known to be correlated with these medical conditions, more precise analysis and quantification of the particular electrical signals produced by sympathetic nerves is needed before a measurement of sympathetic nerve activity can become a useful diagnostic or prognostic tool. Deficiencies in current technology result in either poor autonomic signal quality or present some difficulty in integrating implantable and external electronic enhancements (like telemetry, on-chip amplification, storage memory, and motion sensors).

Chen, et. al. U.S. Pat. No. 10,448,852 discloses a system and method for monitoring nerve activity in a subject, which patent is herein incorporated by reference. The system includes a plurality of electrodes placed in proximity to skin of the subject, an amplifier electrically connected to the electrodes and configured to generate a plurality of amplified signals corresponding to electrical signals received from the subject through the electrodes, and a signal processor. The signal processor applies a high-pass filter to the amplified signals to generate filtered signals from the amplified signals, identifies autonomic nerve activity in the plurality of filtered signals; and generates an output signal corresponding to the filtered signals. The high-pass filter attenuates a plurality of the amplified signals having frequencies that correspond to heart muscle activity during a heartbeat so that only autonomic nerve activity is monitored.

In one embodiment of the process, the monitoring system is configured in a passive operating mode to display the nerve activity on a display device and to record the nerve activity in the memory for analysis by medical professionals. In the passive operating mode, the monitoring system does not activate therapeutic devices nor deliver medicine in an automated manner, although a doctor or other healthcare provider reviews the graphs of nerve activity as part of diagnosis and treatment in a patient. The passive operating mode can be used, for example, during diagnosis of a medical condition, during long-term monitoring of a patient to assess progress in a course of medical treatment, and for studies of subjects during clinical trials or other scientific research.

In addition to monitoring the electrical signals that correspond to the nerve activity and optionally the ECG, Chen uses a signal processor to analyze the signals to identify changes in the level of nerve activity and take an action in response to changes in the nerve activity. For example, the signal processor identifies a change of the nerve activity over time including an average amplitude and variation of the electrical signals that correspond to the nerve activity. The signal processor generates an output of the nerve activity and optionally the ECG with the visual output device, and stores data corresponding to the recorded signals in the signal data recording device, which is typically a digital data storage device such as a solid-state or magnetic disk. The signal processor generates an alert signal or activates a medical device in response to a rapid increase or decrease in the level of electrical activity. The signal processor identifies a level of nerve activity and/or level of cardiac activity in the electrocardiogram of the subject, and generates an output signal in response to deviations from the respective one or both of the nerve activity and the ECG activity.

Chen has deliberately gated its technology to isolate a certain frequency, and then filter down to the cleanest amplitude for monitoring of the selected frequency. Because electromagnetic waves are characterized both by amplitude and frequency, the "information content" of the signal expressed as a frequency dispersion is lost during Chen's method of dial-in band pass filtering. This could result in a critical loss of information. The disclosed method of machine learning analysis of both amplitude and frequency permits us to study both the amplitude and frequency information content of any afferent signals coming from the ANS.

The monitoring system analyzes the electrical activity in the nerves that innervate the skin to generate a measurement of nerve activity in the subject. In human subjects and many animal subjects, the skin is innervated with many nerves that are part of the sympathetic nervous system. The activity monitoring indicates the level of sympathetic nerve activity in the subject over time, including an average amplitude and expected variation of the activity in the sympathetic nerves near the skin. If the identified nerve activity remains within a predetermined threshold, then Chen's process continues to sample additional signals and monitor the nerve activity in the subject. If the monitoring system identifies a rapid change in the electrical signals corresponding to the sympathetic nerve activity that deviates from the baseline predetermined value by more than a predetermined threshold, then the monitoring system generates an alarm or takes another action in response to the identified change in nerve activity. The alarm signal triggers an implanted electrical stimulation device or medicine delivery device. Changes in the nerve activity can correspond to different medical events, including cardiac arrhythmias. Additionally, in some instances the change in the nerve activity occurs prior to onset of the symptoms of the medical event, and the alarm enables prompt action if a medical event that occurs or will occur in the subject requires action by a medical professional.

The electrical activity in the nerves that innervate the skin correspond to multiple events that occur in the subject. For example, many cardiac arrhythmias are preceded by rapid changes in the level of sympathetic nerve activity and the level of sympathetic nerve activity often remains abnormally high or low during an episode of cardiac arrhythmia. Thus, the nerve activity that is identified and monitored is also referred to as a "NeuroElectrocardiogram" (NECG or neuECG) because the electrical signals identified in the neurons that innervate the skin provide information about the activity in the heart. The monitoring system identifies changes in heart activity using only the NECG signal, while in another configuration, the monitoring system identifies changes in the heart activity using both the NECG and a traditional ECG signal.

The monitoring system monitors the activity in the ECG using the band-pass filtered signals. The signal processor monitors the ECG signals using one or more known monitoring techniques to identify the heart rate and other information about the activity of the heart in the subject from, for example, the QRS complexes in one or more heartbeats that are identified in the ECG signal. The signal processor displays traces of both the nerve activity and the ECG in tandem on the visual output device to enable a doctor or other healthcare professional to view the ECG activity and nerve activity simultaneously. As depicted below, the amplitude of the ECG signal is typically greater than the amplitude of the nerve activity signals, and the signal processor scales the signals appropriately to produce visual output graphs that clearly depict both the nerve activity and the ECG activity. The signal processor also stores both the NECG and ECG data in the signal data recording device for further analysis by a doctor or healthcare professional.

The monitoring system is configured in a passive operating mode to display both the NECG nerve activity and the ECG activity on the display device and to record the NECG and ECG activity in the memory for analysis by medical professionals. In the passive operating mode, the monitoring system does not activate therapeutic devices or deliver medicine in an automated manner, although a doctor or other healthcare provider reviews the graphs of nerve activity as part of diagnosis and treatment in a patient. In the passive operating mode associated with the process, doctors or healthcare providers review the NECG and the ECG in tandem to identify changes in the heart activity and to diagnose heart conditions. The NECG data provide additional information about the nerve activity in the patient that complement and expand on the information provided by traditional ECG monitoring. The passive operating mode can be used, for example, during diagnosis of a medical condition, during long-term monitoring of a patient to assess progress in a course of medical treatment, and for studies of subjects during clinical trials or other scientific research.

The monitoring system identifies a level of activity in the subject using both the data from the monitored NECG activity and the data from the ECG activity. Both the NECG and ECG activity includes average levels of activity in both the nerves that innervate the skin and generate normal activity in the heart of the subject. For example, the NECG includes the average amplitude and expected variation in the sympathetic nerves for the subject, while the ECG includes an average heart rate and an expected variation in times between heart beats. If the monitoring system identifies NECG and ECG signals that are both within a predetermined threshold of the expected activity in the subject then the process continues to sample additional signals and monitor the NECG and ECG activity in the subject.

If either or both of the NECG and ECG activity deviate from the predetermined baseline by greater than the predetermined threshold, then the signal processor generates a signal to activate the alarm, activate the electrical stimulation device, or deliver medicine with the medicine delivery device. For example, a rapid increase in the amplitude of the NECG signal can occur prior to and during an episode of cardiac arrhythmia. In one configuration the signal processor activates the alarm to alert a doctor or other healthcare professional to the onset of a cardiac arrhythmia. In human patients that are at risk of sudden heart failure, an advanced warning of even a few seconds prior to the onset of heart failure can assist doctors in resuscitating a patient. The monitoring system includes the implanted electrical stimulator, and the signal processor activates the electrical stimulator to, for example, pace the heart to counteract the arrhythmia.

It can be understood from the foregoing that Chen creates a record of nerve activity, which a physician can study and possibly analyze to diagnose cardiac events and diseases or even to predict the probability of a cardiac event. Otherwise, Chen's system and method is only a means for monitoring nerve activity or the electrocardiogram, and when it exceeds a threshold set by the physician, to generate an alarm to the physician or to activate a pacemaker to stimulate the heart or a medical pump to dispense a medicament. In all cases, the efficacy and the action undertaken by Chen's system and method is predefined by what the physician has deemed necessary and predetermined as normal or requiring no action.

What is needed is a method and system whereby Chen's monitoring of nerve activity can be intelligently mediated by artificial intelligence or machine learning not dependent on the intervention or analysis of a physician. This has several potential advantages that include: continuous, rapid, real-time data acquisition and processing, the ability to dynamically vary band-pass filtering to sample a wider dynamic spectrum of nerve activity, and the possibility of acquiring and simultaneously analyzing more than one nervous system activity marker. The latter would open up the possibility of identifying new, previously unrecognized nervous system outputs with diagnostic and/or therapeutic importance. For instance, the combination of two nervous system outputs analyzed simultaneously with diagnostic and/or therapeutic value that individually have no such use.

BRIEF SUMMARY

The illustrated embodiments of the invention include a method of therapeutically treating a subject comprising the steps of sensing sympathetic nerve activity; communicating the sensed sympathetic nerve activity to a processor; using machine learning in the processor to identify input data sets, $W_i$, correlated to a physiological end point in the subject by processing the input data input sets, $W_i$, to experientially optimize an algorithmically defined physiological goal defined in output data sets by the machine learning; and dynamically controlling a therapeutic device in real time with the processor using the output data sets to treat the subject mediated by the therapeutic device by establishing or tending to establish the physiological end point in the subject.

The step of using machine learning includes the step of comparing instantaneous input data to continuously updated archived input data to determine a unique input data set, $W_i$, that is most likely to result in the physiological end point at the time of comparison.

In one embodiment the physiological end point is blood pressure, e.g. systolic blood pressure, diastolic blood pressure, or mean arterial pressure as dynamically affected by exercise by the subject.

The step of using machine learning includes the step of using a wavelength filter combination that correlates with exercise intensity to process the input data sets sensed between heart beats.

The step of using machine learning includes the step of identifying a unique wavelength filter combination to measure sympathetic nervous system output for rate modulation of a pacemaker.

The step of using machine learning includes the step of identifying a unique wavelength filter combination to treat DRH and HFpEf using PressurePace™ AI to produce the BaroPace™ algorithmic control as defined in PCT/US19/59703. Term "PressurePace" is defined in this specification as the methodology disclosed in PCT/US19/59703, which is incorporated herein by reference. Further, PressurePace™ is a trademark of BaroPace Inc. of Ashland, Oregon.

The step of using machine learning includes the step of identifying a unique wavelength filter combination to identify a wavelength filter combination to "know" when the patient with a pacemaker is exercising, and how intense the exercise is to improve pacemaker rate modulation.

The step of sensing the sympathetic nerve activity includes the step of sensing during the electrically quiet period between heartbeats, when the pacemaker is not pacing, to measure nearby autonomic nervous system.

Another embodiment of the invention includes a method for controlling a pacemaker which includes the steps of sensing the activity of the parasympathetic or autonomous nervous system (ANS), specifically including the vagal nerve, either from a peripheral (skin or otherwise) sensor, or directly from an electrode in or near the heart, such as a pacemaker lead or other in vivo sensing element connected internally or externally to the pacemaker; and data processing the sensed activity of the parasympathetic or autonomous nervous system (ANS) to generate a cardiac control signal for use in the pacemaker.

The step of sensing the activity of the parasympathetic or autonomous nervous system (ANS) includes the steps of sensing the ANS through a base station wristwatch sensor communicated to a pacemaker to generate a corresponding base station processed output signal used by AI to control the pacemaker, and sensing the ANS through a peripheral sensor communicated to the base station wristwatch sensor to generate a corresponding peripheral sensor processed output signal used by AI to control the pacemaker.

The step of data processing the sensed activity of the parasympathetic or autonomous nervous system (ANS) to generate a cardiac control signal for use in the pacemaker includes the step of combining analysis of processed ANS signals from the base station wristwatch sensor and analysis of at least one other peripheral sensor.

Still another embodiment of the method for controlling a pacemaker includes the steps of generating a calibration signal from a standard generator or physiological sample; amplifying the calibration signal; selectively bandpass filtering the amplified calibration signal according artificial intelligence or operator control to obtain an optimal signal for a selected cardiac state; amplifying the optimal signal to obtain a signal strength indicator, a frequency indicator and/or ECG timing indicator of a cardiac function or dysfunction; and communicating the processed and amplified optimal signal to a pacemaker control circuit.

The embodiments include a method where a raw ANS signal is received and processed according determinations derived from the processed calibration to reiteratively determine the processed optimal signal through selective control of bandpass filtering using the signal strength indicator, the frequency indicator and/or ECG timing indicator of a cardiac function or dysfunction, and amplifying the reiteratively determined the processed optimal signal and communicating the amplified reiteratively determined the processed optimal signal to a pacemaker control circuit.

The scope of the embodiments include a method of controlling the rate modulation of a cardiac pacemaker using a right atrial pressure (RAP) sensor including the steps of controlling the pacemaker during first selected conditions using a standard RAP algorithm; and controlling the pacemaker during second selected conditions using PressurePace algorithms.

The first selected condition is a default condition where standard rate modulation is always applied, but in the second selected condition standard rate modulation is turned off and replaced with PressurePace rate modulation or a blend the two, when ANS discrimination becomes active, defined as "blended hierarchal software with PressurePace in the primary control position".

The first selected condition is a default condition where standard rate modulation is not applied and where the second selected condition is where standard rate modulation and PressurePace are combined, blending or alternating the application of the two types of rate modulation algorithms according to how the range of rate modulation settings available is learned through machine learning.

Another embodiment includes a method of any one of the above embodiments further including the steps of: sensing and storing an ANS data set in a mobile monitor; downloading the stored ANS data set into a computer; selectively filtering and processing the downloaded data to generate an AI-based pacemaker control algorithm; and uploading the AI-based pacemaker control algorithm into a programmable pacemaker.

The method further includes the step of repeating the steps of sensing and storing, downloading, selectively filtering and processing, and uploading with multiple ANS data sets over time for a patient to generate a final AI-based pacemaker control algorithm.

The method further includes the steps of sensing and storing ECG and other cardiac and vascular data with the ANS data and/or patient entered event notes with the ANS data sets.

In another embodiment, an improvement in a rate modulation method in a pacemaker implanted into a patient subject to exercising includes the step of modifying the rate modulation method to include machine learning, wherein the pacemaker performs machine learning controlled by a software subroutine that learns the patient's exercise profile and then updates the rate modulation programming on the fly.

The scope of the invention also extends to using any one and all of the above methods on or in a system or apparatus for operating a therapeutic device and other kinds of devices, such as operating or controlling a cardio-defibrillator, a pain-control nerve stimulator, a central nervous system drug delivery system using an implanted reservoir and pump, the same for treating certain forms of diabetes. For example, one other such device includes a stand-alone smart watch with this capability that notifies the wearer of nerve activity that predicts a near-term cardiac arrhythmia to occur, such as atrial fibrillation. Thus the system warns of an impending event. While the apparatus and method has or will be described for the sake of grammatical fluidity with functional explanations, it is to be expressly understood that the claims, unless expressly formulated under 35 USC 112, are not to be construed as necessarily limited in any way by the construction of “means” or “steps” limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
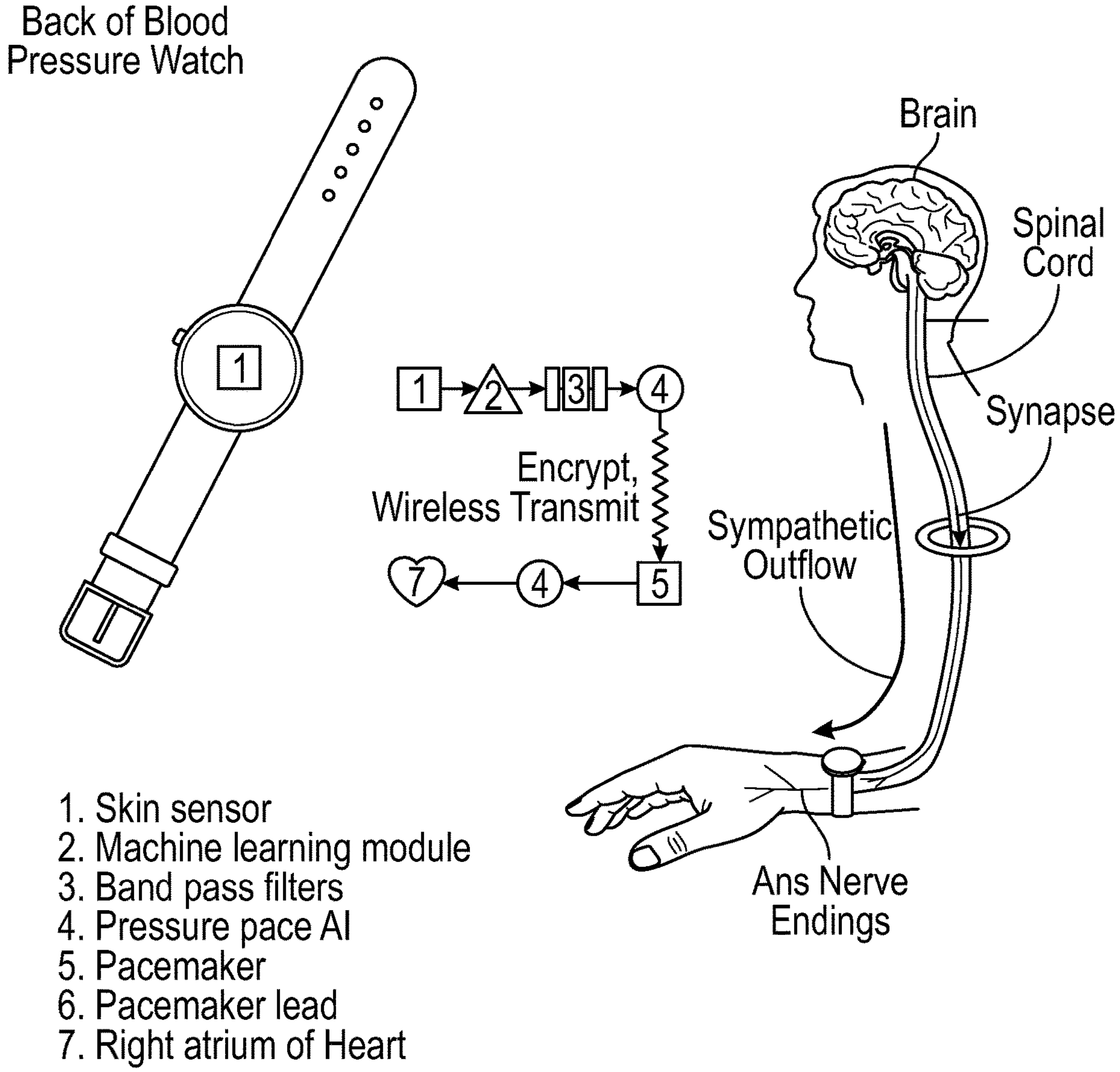
FIG. 1 is a collection of block diagrams of functional elements of the illustrated embodiment wherein the illustrated method of machine learning to control the use of sympathetic nerve activity for cardiac mediation is achieved.

FIG. 1 is a collection of diagrams including a blood pressure watch with a skin sensor 1 disposed on its back which is in contact with the skin of the wrist proximate an autonomic nerve system (ANS) nerve ending. The sensed ANS signal from the skin sensor 1 is input to a processor in the watch in which machine learning 2 is applied to the input signal. The ANS signal arises in the patient’s brain and is correlated to his or her physiological state. The processed signal is then band pass filtered by a collection of filters 3 and amplified as discussed by Chen above. The processed and filtered signals are provided as input to BaroPace™ artificial intelligence processing 4 to generate a control signal. BaroPace™ is a tradename and trademark of BaroPace Inc. of Ashland, Oregon. The control signal is then wirelessly communicated to a pacemaker 5, which responsively generates a cardiac stimulus or response communicated through pacemaker lead 6 to the right atrium of the heart 7. The same system could be used to perform defibrillation, i.e. the action of cardio-defibrillator device, which is usually carried out by a pacemaker lead in the right ventricle, although the defibrillation electrodes can be positioned in any chamber of the heart.

A. Signal Extraction.

Before turning to the illustrated embodiments of the invention, first consider the prior art approach in more general terms. Chen et al. reasoned that the output of the sympathetic nervous system should be responsible for cardiac rhythm disturbances, and therefore that modulating it in some way could be therapeutic. What was first needed was a means to measure the sympathetic nervous system “output” and the prior art looked at the well-known galvanic skin response for this output. To do so, one or more conductive pads are placed against the skin to register electrical potentials that are proportional to known higher level stimuli, such as stress or a change in temperature. The signals are amplified and sampled. The question then becomes if a particular wave length of that sympathetic nervous system outflow correlated with stimuli related to various bodily functions. The signal is highly complex with many layers of noise. Chen used conventional band pass technology to sequentially filter out one noise layer at a time until he arrived at a signal waveform that reproducibly correlated with a physiologic endpoint of interest. That particular combination of sequentially applied band pass filters is the basis of U.S. Pat. No. 10,448,852. Electromagnetic signals are characterized not only by amplitude, but by frequency. The band pass filters are gated by frequency and amplitude is the “gain.”

An analogy helps to explain how we can significantly improve the prior art technology. The search for extraterrestrial intelligence (SETI) is in many ways the same process, sifting through layers of electromagnetic waves trying to find something unique or intelligible. The original approach was to use layered band pass filters to dissect out discrete wavelengths as the prior art has done with nerve activity.

Figure 2:
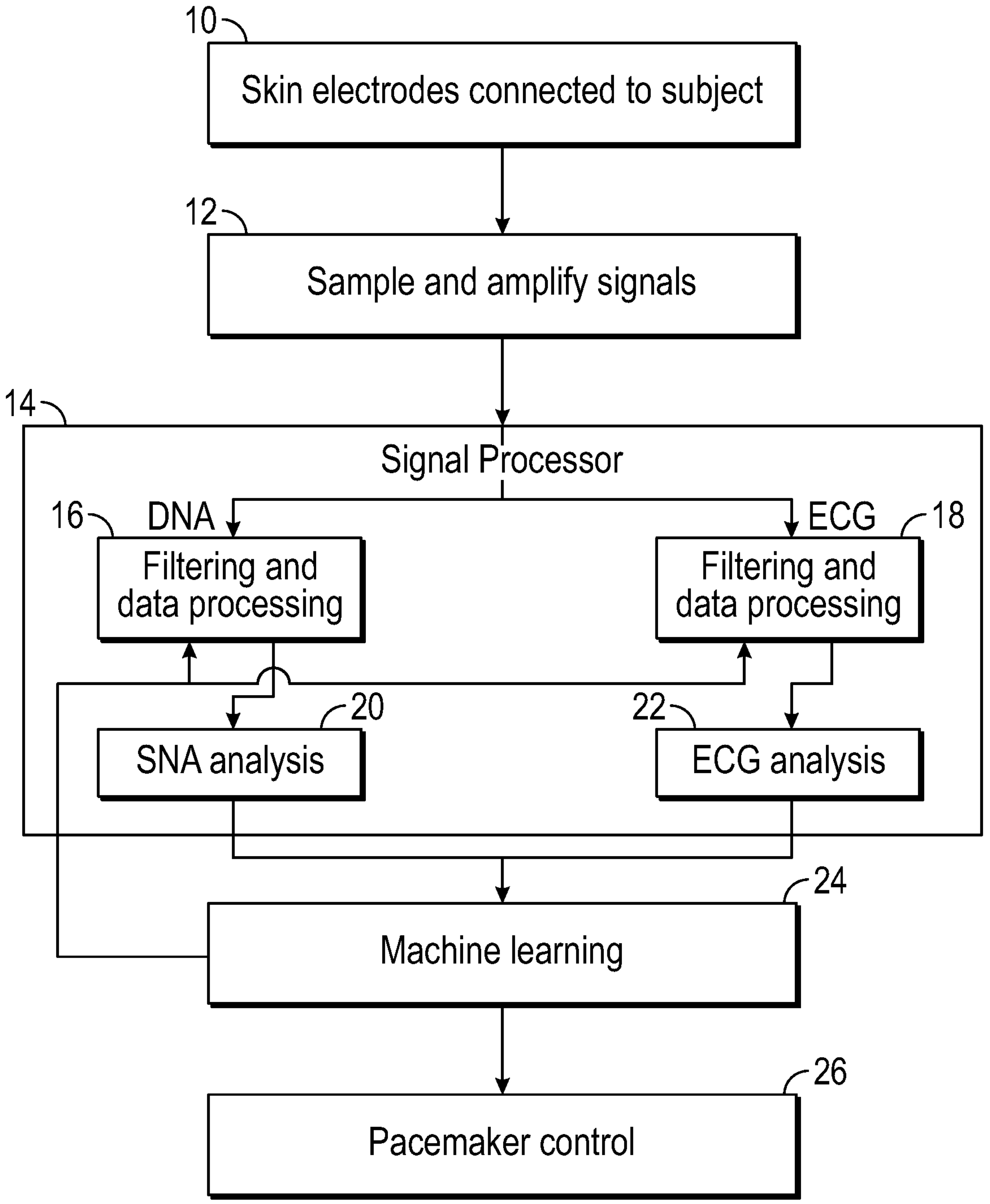
FIG. 2 is a flow diagram of the method performed by the system illustrated in FIG. 1.

Turning to FIG. 2 which depicts an illustrated embodiment of the current invention, one or more conductive pads are placed at step 10 against the skin to register electrical potentials that are proportional to known higher level stimuli, such as stress or a change in temperature. The signals are amplified and sampled at step 12. The sampled and amplified sensed signals, sympathetic nerve activity (SNA) and electrocardiogram activity (ECG) are then input into a signal processor at step 14. Both the SNA and ECG signals are subjected to selective frequency and other filtering and/or other kinds of data processing algorithms at steps 16 and 18, respectively, and the processed data results are subjected to data analysis at steps 20 and 22, respectively. Hence, a particular state or status of the SNA and/or ECG signal can be identified. The input SNA and ECG data inputs, as a data training set, are subject to machine learning at step 24. The data processing at steps 16, 18 and analysis at steps 20, 22 can be modified according to the machine learning step 24 to reformulate the processed input data to determine a cardiac state (or operate an insulin pump), which is then used to control the operation of a pacemaker at step 26 to mediate the identified cardiac state. The process is dynamic and continuously updated, so that if the determined pacemaker operation does not advance toward the desired mediation of the cardiac state, the processing and analysis of the input data is reformulated by means of machine learning to more likely control the pacemaker operation to achieve the desired mediation of the cardiac state.

AI or digital filtering/processing techniques are also used to create a 'blanking period' during the pacemaker initiated electric signals, which are orders of magnitude (volts) larger than cardiac signals (mV) and the yet smaller sympathetic nerve signals (0.02-0.08 mV) which are about one tenth the amplitude of the cutaneous ECG signal. The relevant analysis that we perform "blanks" or "ignores" a window that is about 0.4-1.0 msec in duration, i.e. the typical pulse width of a pacemaker impulse. Also, our hypothesis is that cutaneous recording of nerve activity mirrors stellate ganglion nerve activity, and hence is a reliable measure of sympathetic tone.

The known method of finding a wavelength of interest can be expressed as:

$$\text{Wavelength of interest, } W_i = W_{total} \text{ (all measurable existing wavelengths)} - W_1 \text{ (first wavelength not of interest)} - W_2 - W_3 - \ldots - W_n \text{ (all various wavelengths bearing noise)} \quad \text{A.}$$

A Machine Learning method can be expressed as:

$$W_{total} \rightarrow \text{Machine Learning algorithm} \rightarrow W_i \quad \text{B.}$$

Machine learning (ML) relates to the use of computer algorithms that improve automatically through experience. It is seen as a subset of artificial intelligence. Machine learning algorithms build a model based on sample data, known as "training data", in order to make predictions or decisions without being explicitly programmed to do so. Machine learning algorithms are used in a wide variety of applications, such as email filtering and computer vision, where it is difficult or unfeasible to develop conventional algorithms to perform the needed tasks. The detailed operation of what takes place in the machine learning black box processor may be currently poorly understood in detail, but it is characterized by a relentless experimentation with or training of the data input sets to optimize an algorithmically defined goal defined in output data sets. The analysis process externally is fairly basic. Feed the black box a sample of a desired data output, such as a fall in blood pressure, plus the data input set, $W_{total}$. Then give the machine-learning black box or program access to all possible filters or other data processing tools, and allow the machine-learning program to process the input data signals until it learns which combination yields the highest probability of finding the wavelength(s) ($W_i$) that correlates with a physiological endpoint of interest, such as blood pressure.

This control method is very different than prior methods which are based on physician derived alarms relative to predefined baselines of nerve activities. The prior method is a physician-defined parametrically controlled method by which an alarm is generated when a previously defined data parameter is exceeded to prompt physician intervention or automatic dispensation by a drug pump. Moreover, it is possible that the nervous system output ($W_i$) which needed the correct data input sets are not the same as those that the prior art identifies using a combination of filters.

According to the illustrated embodiments of the current invention, the input data sets, $W_i$, needed or useful for blood pressure is or are different than the input data sets, $W_i$, for cardiac arrhythmias. The needed input data sets, $W_i$, will likely be not one wavelength, but a specific combination of a family of wavelengths that describe an individual effect, such as lowering blood pressure as opposed to a decrease in atrial action potential threshold or other cardiac parameter.

B. Making Use of the Extracted Signal, $W_i$

Once the artificial intelligence identifies the $W_i$ for blood pressure, then the task becomes how to use it. At each discrete point in the therapeutic algorithm, besides the need to make decisions very rapidly, there are too many possible permutations of the data set to make that decision linearly or by conventional medical analysis by a physician.

Suppose at any moment in time a subject's physiologic state is characterized by the subject's blood pressure, systolic and diastolic, the heart rate, and the sympathetic nerve activity output ($W_i$). Some combination of that input data will be used to decide whether to increase heart rate, decrease it or leave it the same using a pacemaker. In addition, that decision will be made by comparing the instantaneous data to archived data that is continuously updated in order to determine the unique parameter set that is most likely to result in the desired physiologic response at a moment in time. Added to this is the complexity of exercise which requires a different blood pressure response than the steady state blood pressure. The possible permutations of input data sets would be a long multiplication function of the discrete variables, each with three possible endpoints. Artificial intelligence is the only practical method to sort out the solution from the characterizing input data sets.

Current pacemakers use two sensor inputs to "know" when the patient has begun exercise and when rate modulation should be activated, specifically these sensor inputs are provided by a motion sensor and a respiratory rate monitor which senses diaphragmatic movement. Exercise also increases the sympathetic nervous system output and is a further indicator of exercise. Current rate modulation is programmed empirically. The device only self-adjusts for different levels of activity on the basis of the degree of motion reported by the motion sensor, or how fast the subject is breathing, and only then within the empirically pre-determined ranges for several physiologic variables, including but not limited to: heart rate acceleration with exercise, heart rate deceleration after exercise, and maximum and minimum heart rate.

The industry has failed to consider modifying the rate modulation to include machine learning, whereby the pacemaker contains a machine learning software subroutine that "learns" the patient's exercise profile and then updates the rate modulation programming on the fly. Current rate modulation is adjusted in the doctor's office and not in the pacemaker. Such a pacemaker method is greatly enhanced if it also includes blood pressure regulation.

AI as described above is used to sort out the nervous system output from either a skin sensor or from the passive phase of the pacemaker electrodes between heart beats via wavelength filter combination found by the AI that best correlates with exercise intensity. Using AI to identify a unique wavelength or add a frequency filter combination to measure sympathetic nervous system output for rate modulation of a pacemaker is a problem solving approach which materially modifies the prior art approach. The identified wavelength filter combination is then usable to treat DRH and HFpEf using PressurePace$^{AI}$ as defined in PCT/US19/59703 incorporated herein by reference. Using AI to find the unique or best wavelength filter combination to "know" when the patient with a pacemaker is exercising, and how intense the exercise is to improve basic pacemaker rate modulation comprises a material advance in the art.

Further, using the electrically quiet period between heartbeats, when the pacemaker is not pacing, to measure nearby autonomic nervous system activity by the same method used for a skin sensor according to prior art is an improved insight into pacing not previously practiced.

Using Machine Learning/AI to define the input data sets, $W_i$, and process them for a complex physiologic endpoint used in a real-time dynamic manner defines a significantly new and important improvement needed to make the prior art Chen system and method useful and to realize its potential capability.

It can now be appreciated that the above disclosed embodiments are an improvement over the art in that the method of sensing sympathetic nerve activity is performed using machine learning/AI, which has the added advantage of considering all possible combinations of, and all possible sequencing of the filtering process, including using more than one filter combination in short sequences. The method and apparatus of the disclosed embodiments process raw data derived from surface or skin electrodes that sample the electrical signals sensed from central nervous system activity in response to a known stimulus, and determine one or more unique electrical frequencies or wavelengths using AI/machine learning algorithms to monitor the response, calibrate it, and form the basis of feedback inhibition to the nervous system. The disclosed embodiments create a real-time dynamic autonomous feedback loop that continually adjusts nervous system feedback inhibition for an optimal effect.

The disclosed embodiments can also use and record non-electrical signals, such as sound or heat signatures, to induce or calibrate a nervous system response for the purpose of detecting and/or calibrating a feedback inhibition for a defined therapeutic effect.

The disclosed embodiments use a cardiac electrode which could be an ECG-like electrode on the skin, or one of the pacemaker leads internally, as the sensing or stimulating element and apply the stimulus during the quiet period of the cardiac cycle, either with predetermined timing, or several stimuli in sequence using the BaroPace™ algorithm. Hence, the disclosed embodiments employ the BaroPace™ stimulus architecture algorithm to deliver an optimal frequency, amplitude, timing, and sequence of multiple stimuli. For example, an optimal magnitude of an individual stimulus is either a pacing level stimulus, or a sub-threshold stimulus, which is performed in a combination in a predetermined sequence, such as first a supra threshold stimulus followed by a subthreshold stimulus during the quiet period.

The disclosed embodiments provide for cardiac pacing via a standard pacing electrode or newly design pacing electrode adapted to sympathetic nerve stimulation or near-cardiac ganglia to apply a pacing stimulus at a subthreshold amplitude alone or in combination with other pacing stimuli, or a subthreshold stimulus to produce nervous system inhibition, or a non-nervous system effect such as stimulated release of atrial naturietic peptide or other tissue factor related to a hemodynamic effect. The prior art discussed above assumes that the result of their ganglionic stimulus method is a nervous system feedback. The disclosed embodiments contemplate a feedback that is not related to the nervous system.

The disclosed embodiments illustrate how to adjust stimulus strength and stimulus architecture or protocols to produce an optimal feedback effect for a specific endpoint that is not cardiac rhythm disturbances, such as a reduction in blood pressure.

The disclosed embodiments add or layer more than one sensor input or add more than one type of stimulation using artificial intelligence to one or more locations on the body using one or more types of stimuli. The central nervous system is inhibited in response to more than one stimuli or inputs, which include blood pressure and the patient's subjective report of symptoms.

The disclosed embodiments control cardiac pacemaker rate modulation by adding a new measure of exercise intensity via monitoring of the central nervous system which does not involve stimulation, instead uses a filtered signal that measures the degree of exercise intensity in a quantitative manner without the inhibition of the nervous system.

Thus, it can be understood that the disclosed embodiment use monitoring nervous system activity to treat DRH and/or HFpEF in combination with BaroPacing or what is defined as PressurePace AI using the disclosed trend analysis, or Stimulus Architecture Algorithm (SAA), as defined and disclosed in "An Intelligently, Continuously And Physiologically Controlled Pacemaker And Method Of Operation Of The Same", International Pat. App. PCT/US20/25447; and "Method of Treatment of Drug Resistant Hypertension by Electrically Stimulating the Right Atrium to Create Inhibition of the Autonomic Nervous System," International Pat. Appl., PCT/US20/44784, incorporated herein by reference.

It can also now be appreciated that the treatment of cardiac arrhythmias is improved using the improvements ofthe disclosed embodiments described above.

A substantial improvement in cardiac treatments is obtained by combining the nervous system sensing of the discussed prior art with BaroPacing to treat a patient including the use of a class of drugs, that without BaroPacing does not produce a therapeutic response. At the same time this improvement includes the elimination of one or more drug classes that currently are in use to further improve treatment benefits. For example, treating a patient with ACEI/ARB provides a therapeutic drug effect not present without BaroPacing, and removes the adverse effects on heart rate modulation experienced with beta blockers, which are eliminated from the treatment protocol.

The illustrated embodiments also extend to sensing the activity of the parasympathetic or autonomous nervous system (ANS), specifically including the vagal nerve, either from a peripheral (skin or otherwise) sensor, or directly from an electrode in or near the heart, such as a pacemaker lead or other in vivo sensing element connected internally or externally to the pacemaker.

Figure 3:
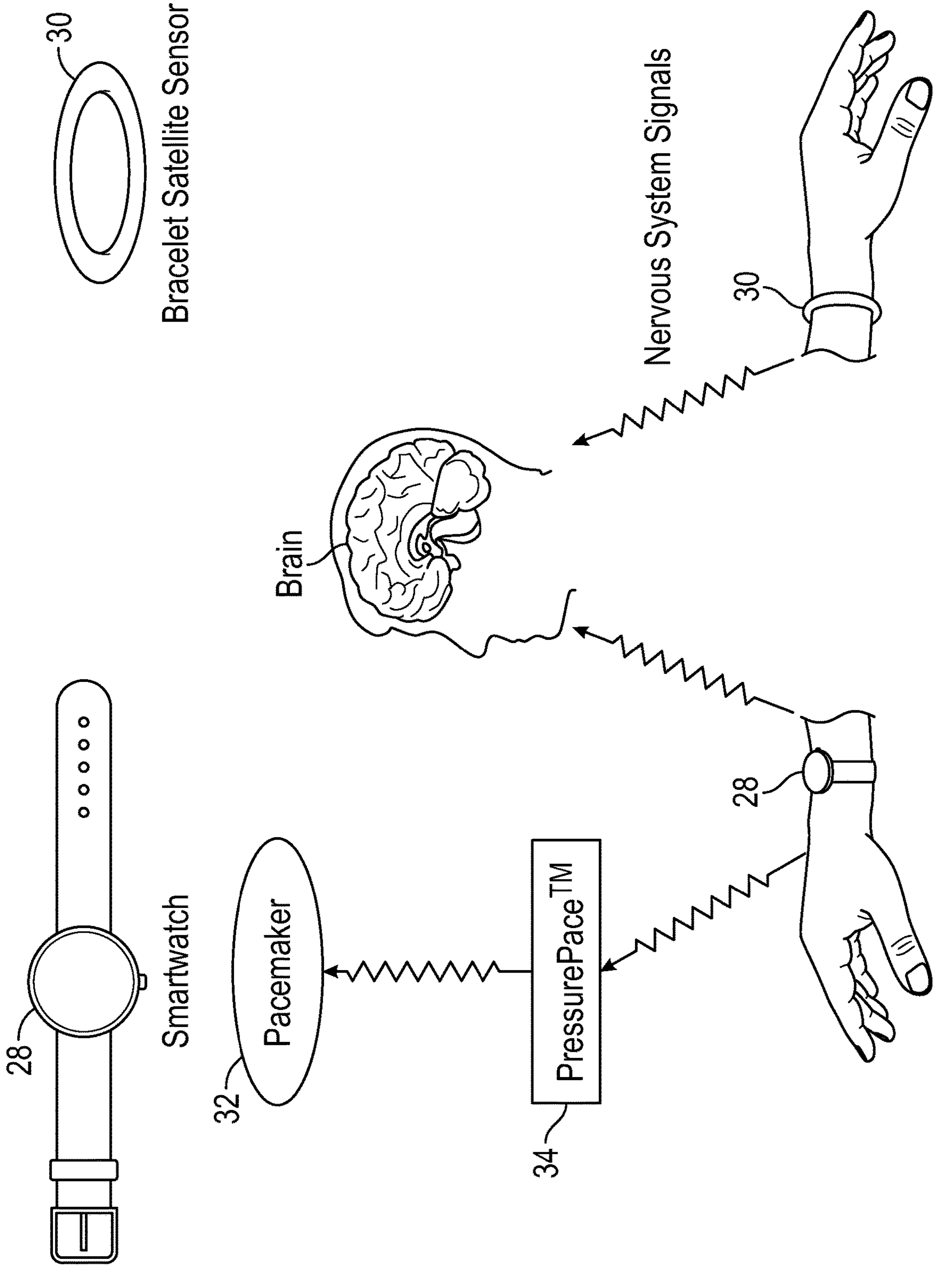
FIG. 3 is a diagram showing the use of peripheral sensors in combination with a main wristwatch base station/sensor used for a system of pacemaker control.
Figure 4:
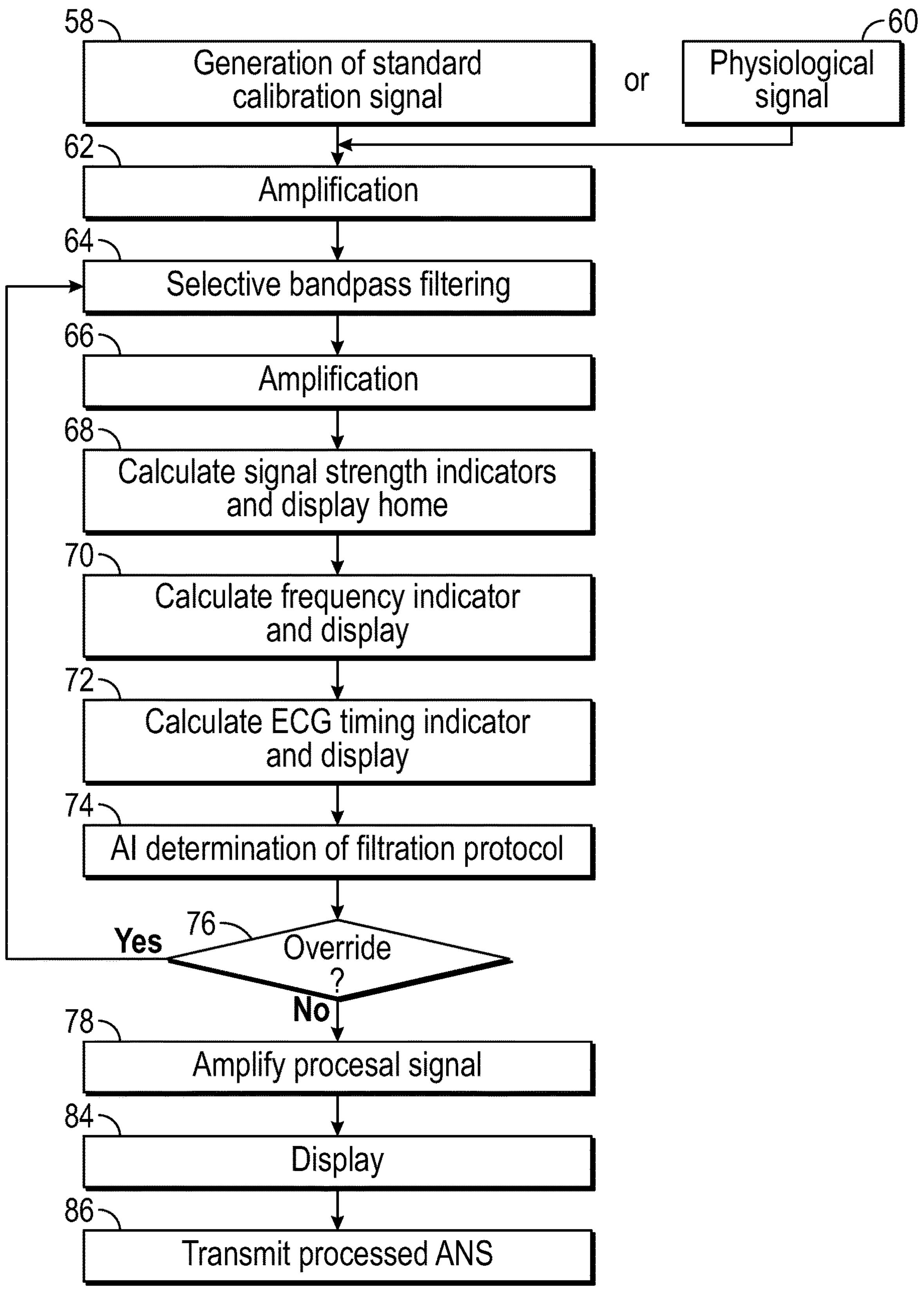
FIG. 4 is a flow diagram of the operation of the system of FIG. 5.
Figure 5:
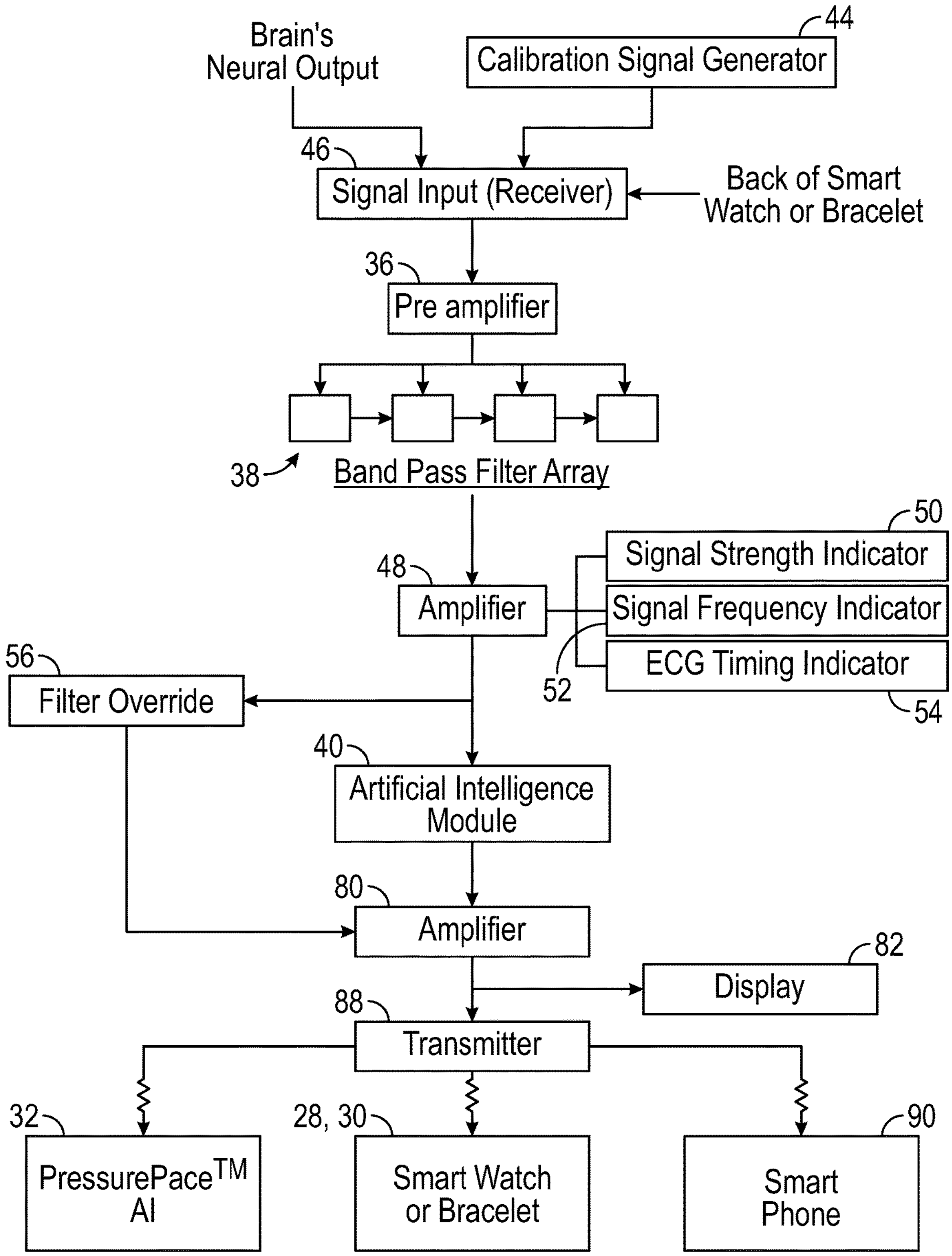
FIG. 5 is a block diagram of the illustrated system which operates according to the flow diagram of FIG. 4.

Turning to FIGS. 3-5, another embodiment of the current invention is illustrated. This embodiment is resident in a smart watch primary sensor station 28, or in one or more peripheral sensor stations 30 linked to the primary station 28 via a Bluetooth or other wireless communication link. In the preferred embodiment, the functionality and circuitry/components herein described are resident in the primary sensor station 28.

A Bluetooth data link for the sensor to an app or between a satellite bracelet app and a smartwatch or other repository of the processing software is subject to a 300-millisecond transfer delay in the Bluetooth signal. Thus, instead of a Bluetooth data signal, radio waves of higher frequency with no delay may need to be used, which is conventional with the realtime transmission of ECG signals.

Figure 6:
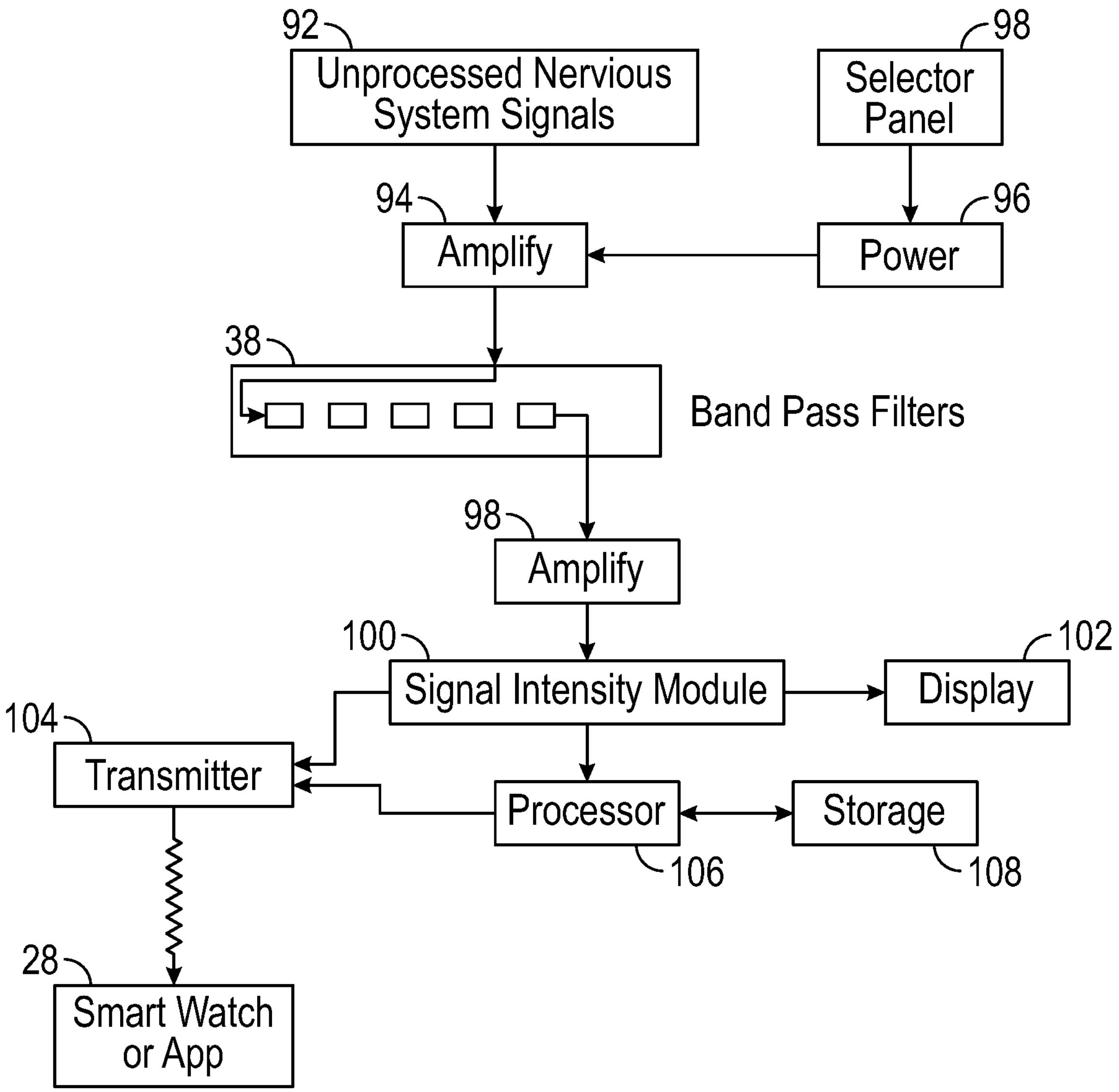
FIG. 6 is a block diagram of the elements included in a peripheral sensor used in combination with a base sensor.

Before considering the system in greater detail, first turn your attention to the peripheral sensor station 30 to monitor the central nervous system activity as schematically illustrated in FIG. 6. The advantage of including a peripheral sensor station 30 is to increase signal sensitivity and increase signal specificity. The disclosed embodiment does not add additional "dumb" sensors to the existing system as is the case for prior art monitoring systems. For instance, the commercial product in use by the KardiaCor mobile app is a three ECG electrode system wirelessly connected to a phone app that processes the signal received from up to three dumb sensors to generate an ECG.

The added peripheral sensors 30 have processing capabilities as shown in FIG. 6. One embodiment includes a bracelet 30 worn on the wrist opposite to the arm with a blood pressure smartwatch 28 as seen in FIG. 3. This bracelet sensor 30 functions to: receive the raw signal through a skin contact sensor 92 included in or on bracelet 30; amplify the raw signal by amplifier 94 powered from source 96 and controlled by selector panel 98 included on or in bracelet 30; process the signal by passing it through one or more band pass filters that are part of an array 38 that divides the useful frequency spectrum into defined blocks which can be selected individually or in combination by a human operator or AI. The selectively filtered data signal is then amplified into a refined data signal by amplifier 98. If the operator or the AI determines with module 100 that the signal intensity for the processed data signal is optimal, then the intensity is displayed in display 102 and transmitted through means of transmitter 104 to the smartwatch 28. Module 100 is communicated to a processor 106 and memory storage 108, which controls the process for transmission and archives the accepted data. If the processed data signal is determined to be non-optimal, in any way, the process is terminated and the operator is prompted to reposition the sensor 30 and repeat the foregoing steps.

Another embodiment could add a third sensor of the same type as the wrist bracelet 30 for use on the ankle to further increase three-dimensional signal acquisition.

Another embodiment could add an AI module in the system of FIG. 6 to make automatic decisions during the process, such as selecting the optimal band pass filter combination in the array 38 to process the signal.

Figure 7:
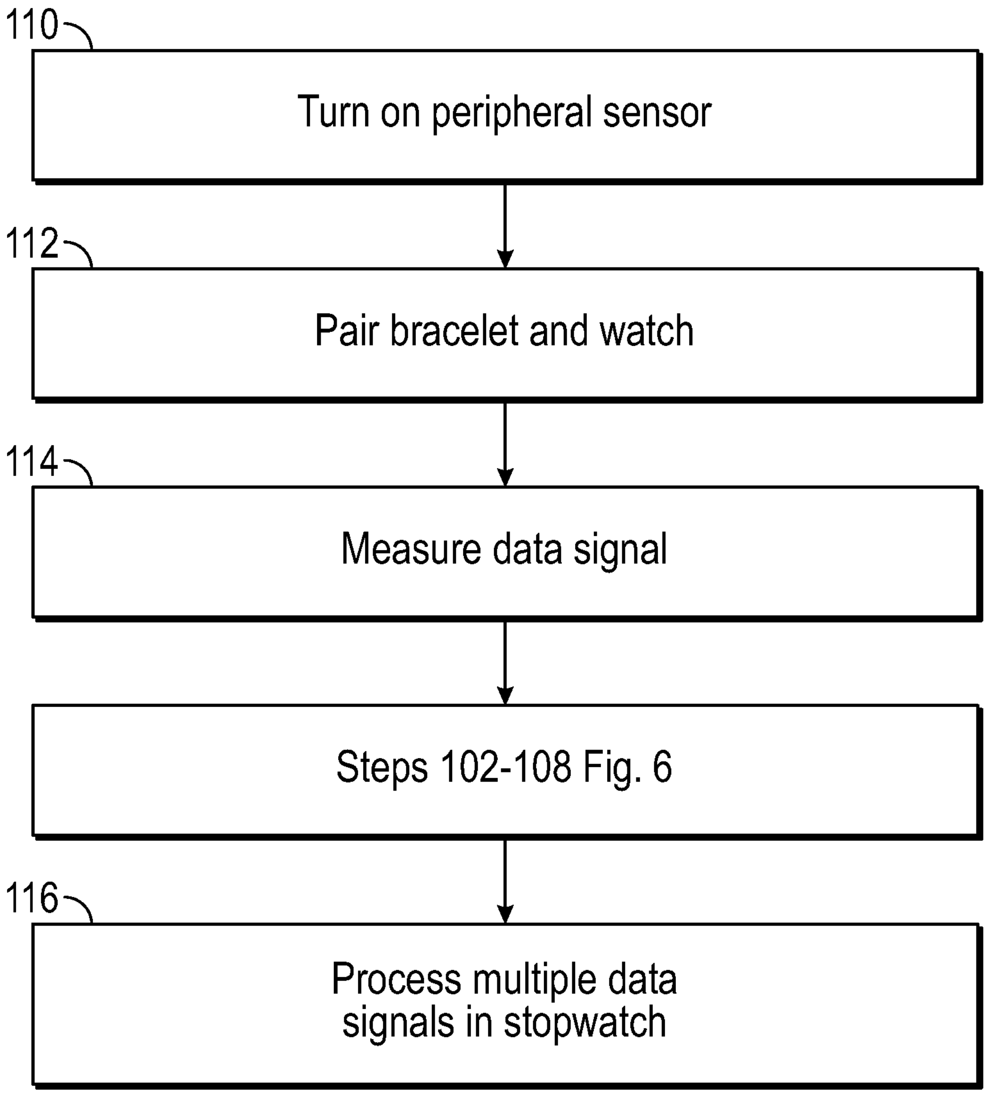
FIG. 7 is a flow diagram illustrating the operation of the peripheral sensor of FIG. 6.

Consider now how the process would be performed as shown in FIG. 7 using a peripheral sensor 30. The power is first turned on in the peripheral sensor at step 110. The bracelet 30 is then paired or synched at step 112 to the smartwatch 28. The operator selects a data signal type to be collected and analyzed at the smartwatch 28. This information is transmitted to the bracelet 30 as part of the pairing process in step 112. The operator has the option to select the filter combination for a desired signal type, or to allow the AI to make the selection in concert with the smartwatch 28. The measurement takes place at step 114 at the smartwatch 28 and at one or more satellite sensors 30, such as the bracelet on the opposite wrist or ankle. The result of the combination of the data inputs from the various paired peripheral sensors 30 is analyzed at the smartwatch 28 at step 116 after being processed through steps 92-108 as described above and shown in FIG. 6. All the data streams can be transmitted to the PressurePace™ app 34 to regulate pacemaker control, or for use by a clinician as a stand-alone measurement to predict or treat a specific disease state.

Return now and consider the system of FIG. 5 operating as illustrated by the flow diagram of FIG. 4 and as described below. ANS signals are sensed through skin contacts by station 28 and communicated to a programmable pacemaker 32 including PressurePace software 34. The ANS signal must first be calibrated. There are two methods of calibration:

In the first method of calibration, a calibration signal of known amplitude, frequency, and ECG-timing is sent to a pre-amplifier 36 through signal input receiver 46 shown in FIG. 5. The amplified signal is sent to a programmable band pass filter array 38 for processing. The filter array 38 passes the signal through the array 38 in a sequence, which is either pre-selected, or determined by the AI module 40 in FIG. 5 after a period of machine learning. In the case of a calibration step, the AI module 40 determines a sequence or configuration of the filter array 38 that most optimally results in a reproducible calibration signal with satisfactory variance. The resulting signal is amplified by amplifier 48 and displayed in a signal strength indicator 50, signal frequency indicator 52, and electrocardiographic timing indicator 54. An override control 56 is available to preselect the band pass filter combination and sequencing in array 38. The calibration signal is used to "teach" the AI module 40 to find the same signal (amplitude, frequency, electrocardiographic timing) in a raw ANS signal.

In the second method of calibration, a subject or patient with a known physiologic marker of interest, such as hypertension or atrial fibrillation is monitored by the functioning system and the system collects full spectral data, which is archived. The archived data is processed by the AI module 40 using machine learning. Machine learning correlates the desired physiologic or electrocardiographic marker with the spectral data, sifting out the signal properties that best correlate with the presence of that signal in a quantifiable manner. The filter combination/sequence of array 38 that best extracts the signal of interest becomes the filter combination/sequence for the subject patient, or can be preselected for other subjects searching for the quantifiable presence of electrocardiographic timing of the same marker omitting the calibration process for the new subject.

Consider now the methodology in greater detail. The basic system is comprised of a smart watch 28 with a skin electrode similar to an ECG electrode and one or more peripheral sensors 30 wirelessly linked thereto. In the preferred embodiment, the smart watch 28 functions as the primary sensor platform with one peripheral sensor 30, such as a bracelet worn on the opposite wrist as shown in FIG. 3. This increases the spatial vector of the signal input to improve signal acquisition.

For an individual patient, system functioning can commence as disclosed above in the first calibration type based on a standard input calibration signal. The second calibration type is followed in the same individual patient by autonomous function using the previously derived optimal filter combination/sequence of array 38 corresponding to that patient, or using an autonomous function in a separate subject based on a filter sequence that is pre-selected.

By way of review, the method performed by the system of FIG. 5 can be illustrated in the flow diagram of FIG. 4. Calibration signal generator 44 generates at step 58 a pre-selected signal of known amplitude, frequency, and timing with reference to the electrocardiographic cardiac cycle as a first possible initial data input. The initial data input is either the calibration signal from generator 44 or a real-time physiologic signal sensed at step 60 through an ECG-like electrode skin contact in watch 28. Pre-amplifier 36 receives the signal from either step 58 or 60 and amplifies it at step 62. Discrete band pass filtering by array 38 is performed at step 64. Band pass filter components in array 38 are selectively gated to exclude all but a specific range of the electrical spectrum in the signal from step 58. The amplified input signal from step 60 can take any permutation of multiple paths in array 38, from passing through one filter only, all of the filters in sequence except one, or any permutation thereto. The sequence can be operator preselected, or regulated by an Artificial Intelligence module 40. The filtered signal is amplified at step 66 by amplifier 48 and various signal strength indicators are calculated and displayed at step 68. Similarly, a frequency indicator is calculated and displayed at step 70. An electrocardiographic timing indicator is calculated and displayed at step 72, which determines the timing of the data signal with maximal amplitude, or preselected characteristics in relationship to the electrocardiographic cycle, such as the initiation of the QRS sequence. After a sequence of machine learning, the AI module 40 determines the optimal band pass filter combination and sequence at step 74 to extract the desired data signal. The filter sequencing override control 56 optionally disables the AI module 40 and processes the signal with a preselected filter combination at step 76. The processed signal, by whatever protocol is applied, is amplified at step 78 by amplifier 80, displayed in output circuit 82 at step 84. The processed ANS signal is then transmitted at step 86 by wireless transmitter 88 to PressurePace software controlled circuits 34 in pacemaker 32, to smart watch 28 or bracelet 30, or to an addressed smart phone 90. All components are wirelessly connected and individually powered.

In addition to the foregoing, turn now to consider how the methodology of PressurePace integrates with standard rate pacemaker modulation, or prior art rate modulation protocols used in pacemakers. Rate-modulated pacing is an advancement in pacing technology that has opened the way for the development of a wide variety of pacemaker generators and pacing modes. Rate-modulated pacemakers use a physiologic sensor other than the sinus node, namely the intrinsically occurring or natural heartbeat. The sinus node (SN) is not a sensor. When it is working the SN generates an electrical pulse that begins propagating through the cardiac tissues from top to bottom and right to left causing a sequential heart beat to adjust the pacing rate according to the physiologic needs of the patient. As rate-modulated pacemakers become more widely used, those caring for patients with these devices need to understand pacing physiology as well as rate-modulated pacing technology to provide optimal patient care.

When using the disclosed system with exercise, the simplest iteration of our PressurePace technology is to have the software "off" or inactive when the patient is at rest, and active when exercise/exertion is "sensed." A later iteration is to have the system active during "rest" as well, but likely with a different pacemaker right atrial pressure (RAP) control algorithm for long-term blood pressure regulation.

There are two different subsets of patients to which the disclosed system is advantageously applied. One group has standard rate modulation turned on all the time, and we turn it off and replace it with PressurePace rate modulation or a blend the two, when our system or ANS discrimination becomes active. This results in a pacemaker sensor-driven by RAP with a blood pressure regulation higher in the control hierarchy with PressurePace taking over when exercise begins. We define this as "blended hierarchal software with PressurePace in the primary control position."

There is a second group of patients where the physician has the rate modulation already off. In such patients the disclosed system turns the rate modulation back on, with the RAP controlled by again by a blended system. In this instance, however, because the rate modulation was previously off, we don't know in advance what the correct rate modulation settings will be. One solution is to have the software activate in phases. For instance, start with PressurePace off, and standard rate modulation on, but in the learning mode. The subject exercises by walking and the system "learns" the range of rate modulation settings available. Then PressurePace is added and it picks the RAP best suiting the blood pressure within the previously defined range of rate modulation settings blending or alternating the application of the two rate modulation algorithms.

The invention may be exploited in another embodiment wherein a high fidelity mobile monitor, senses the ANS signals and stores them, along with other data parameters, like conventional ECG signals, and/or with patient noted events, like exercising, sleeping, stress or the like. The mobile monitor is similar to a Holter monitor used to record ECG signals for a cardiac study of a patient, but in this embodiment, the mobile monitor must be capable of accurately recording signals with a frequency range of 1 Hz-5000 Hz as taught be Chen U.S. Pat. No. 10,448,852, whereas ECG signals. ANS signals generally are in the range of hundreds of Hz to several kHz. The recorded ANS signals are then communicated to the cardiologist's office or the monitor brought in to be downloaded into a computer, where the recorded ANS signals are then processed with the filtration techniques and AI described above to generate a pacemaker control algorithm, which is then uploaded into the patient's pacemaker. The process can be repeated daily to derive an optimal algorithm for the patient using an AI analysis of the recorded filtered ANS and cardiac data until the cardiac or vascular goal is reached. In this manner, a conventional programmable pacemaker not having the filtration circuitry or AI capabilities of the BaroPace AI algorithm can be programmed to become functionally equivalent in operation to the BaroPace AI algorithmic pacemakers described above.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

For example, there are a number of different storage media possible for the sensed and recorded data sets, such as a chip worn under a bandage. The potential uses are far more than that expressly disclosed above. The above technology can be adapted for use in law enforcement in relation to lie-detector methodology, which currently employs the more simple galvanic skin response. ANS sensing could be adapted to the same kind of application.

Further, the technology disclosed above could be used as part of a pharmaceutical screening tool to test drugs thought to influence the sympathetic nervous system. Examples include beta adrenergic blocking drugs of various "flavors", some anti-depressants, and/or cardiac anti-arrhythmic drugs to monitor the potential negative influence of all manner of drugs on the GI track where excess sympathetic or parasympathetic stimulation can adversely affect gut motility, acid secretion, etc.

The technology disclosed above is usable as an adjunct to EEG for seizure diagnosis and therapeutic monitoring.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A method for modifying a therapeutic device setting, the method comprising:

receiving a first sympathetic nerve activity ("SNA") signal, the first SNA signal being generated by an SNA sensor;

receiving a physiological endpoint;

providing the first SNA signal and the physiological endpoint to a machine learning model trained on a training dataset;

analyzing, by the machine learning model, the first SNA signal using one or more wavelength filter combinations to identify a first one or more wavelengths within the first SNA that corresponds to the physiological endpoint;

outputting, by the machine learning model, a subset of the first SNA signal comprising the first one or more wavelengths;

receiving the subset of the first SNA signal from the machine learning model;

determining a first current physiological state based on the subset of the first SNA signal;

determining the therapeutic device setting based on the first current physiological state and the physiological endpoint; and causing a therapeutic device to be modified based on the therapeutic device setting.

2. The method of claim 1, further comprising:

receiving a second SNA signal, the second SNA signal being generated by the SNA sensor;

providing the second SNA signal and the physiological endpoint to the machine learning model;

analyzing, by the machine learning model, the second SNA signal using the one or more wavelength filter combinations to identify a second one or more wavelengths within the second SNA that corresponds to the physiological endpoint;

outputting, by the machine learning model, a subset of the second SNA comprising the second one or more wavelengths;

receiving the subset of the second SNA signal; and determining a second current physiological state based on the subset of the second SNA signal.

3. The method of claim 2, wherein the training dataset comprises the first current physiological state and the second current physiological state.

4. The method of claim 2, further comprising:

determining an updated therapeutic device setting based on the second current physiological state and the physiological endpoint; and causing the therapeutic device to be modified based on the updated therapeutic device setting.

5. The method of claim 1, wherein the subset of the first SNA signal excludes portions of the first SNA signal collected during a blanking period.

6. The method of claim 5, wherein the blanking period corresponds to a duration of time during which the therapeutic device outputs an electrical impulse.

7. The method of claim 1, wherein the physiological endpoint is a target blood pressure.

8. The method of claim 7, wherein the target blood pressure is one of a systolic blood pressure, diastolic blood pressure, or mean arterial pressure.

9. The method of claim 1, wherein the SNA sensor is associated with a wearable device.

10. The method of claim 1, wherein receiving the first SNA signal further comprises:

receiving a sensed SNA signal;

amplifying the sensed SNA signal to generate an amplified sensed SNA signal; and processing the amplified sensed SNA signal using a band pass filter to generate the first SNA signal.

11. A system comprising:

a memory configured to store processor-readable instructions; and a processor operatively connected to the memory, and configured to execute the instructions to perform operations that include:

receiving a first sympathetic nerve activity ("SNA") signal, the first SNA signal being generated by an SNA sensor;

receiving a physiological endpoint;

providing the first SNA signal and the physiological endpoint to a machine learning model trained on a training dataset;

analyzing, by the machine learning model, the first SNA signal using one or more wavelength filter combinations to identify a first one or more wavelengths within the first SNA that corresponds to the physiological endpoint;

outputting, by the machine learning model, a subset of the first SNA signal comprising the first one or more wavelengths;

receiving the subset of the first SNA signal output from the machine learning model;

determining a first current physiological state based on the subset of the first SNA signal;

determining a therapeutic device setting based on the first current physiological state and the physiological endpoint; and causing a therapeutic device to be modified based on the therapeutic device setting.

12. The system of claim 11, wherein the operations further include:

receiving a second SNA signal, the second SNA signal being generated by the SNA sensor;

providing the second SNA signal and the physiological endpoint to the machine learning model;

analyzing, by the machine learning model, the second SNA signal using the one or more wavelength filter combinations to identify a second one or more wavelengths within the second SNA that corresponds to the physiological endpoint;

outputting, by the machine learning model, a subset of the second SNA comprising the second one or more wavelengths;

receiving the subset of the second SNA signal; and determining a second current physiological state based on the subset of the second SNA signal.

13. The system of claim 12, wherein the training dataset comprises the first current physiological state and the second current physiological state.

14. The system of claim 12, wherein the operations further include: determining an updated therapeutic device setting based on the second current physiological state and the physiological endpoint; and causing the therapeutic device to be modified based on the updated therapeutic device setting.

15. The system of claim 11, wherein receiving the first SNA signal further comprises:

receiving a sensed SNA signal;

amplifying the sensed SNA signal to generate an amplified sensed SNA signal; and processing the amplified sensed SNA signal using a band pass filter to generate the first SNA signal.

16. A method for modifying a therapeutic device setting, the method comprising:

receiving the input signals comprising a sympathetic nerve activity ("SNA") signal and an electrocardiogram activity ("ECG") signal;

providing the SNA signal and the ECG signal to a machine learning model trained on a training dataset;

analyzing, by the machine learning model, the first SNA signal using one or more wavelength filter combinations to identify a first one or more wavelengths within the first SNA that corresponds to the EXG signal;

outputting, by the machine learning model, a subset of the SNA signal comprising the first one or more wavelengths;

receiving the subset of the SNA signal output from the machine learning model; receiving a physiological endpoint;

determining a first current physiological state based on the subset of the SNA signal;

determining the therapeutic device setting based on the first current physiological state and the physiological endpoint; and causing a therapeutic device to be modified based on the therapeutic device setting.

17. The method of claim 16, wherein the subset of the first SNA signal excludes portions of the SNA signal collected during a blanking period.

18. The method of claim 17, wherein the blanking period corresponds to a duration of time during which the therapeutic device outputs an electrical impulse.

19. The method of claim 17, wherein the machine learning model is configured to determine the blanking period based on the ECG signal.

20. The method of claim 17, wherein the SNA signal is generated at a first sensor and the ECG signal is generated at a second sensor.

* * * * *